(12) United States Patent
Buzzoni et al.

(10) Patent No.: US 11,840,494 B2
(45) Date of Patent: Dec. 12, 2023

(54) PROCESS FOR TREATING POLYALKYLAROMATIC HYDROCARBONS

(71) Applicant: VERSALIS S.P.A., San Donato Milanese (IT)

(72) Inventors: Roberto Buzzoni, Novara (IT); Giovanni Antonio Fois, Mantova (IT)

(73) Assignee: VERSALIS S.P.A., San Donato Milanese (IT)

( * ) Notice: Subject to any disclaimer, the term of this patent is extended or adjusted under 35 U.S.C. 154(b) by 0 days.

(21) Appl. No.: 17/639,141

(22) PCT Filed: Aug. 21, 2020

(86) PCT No.: PCT/IB2020/057864
§ 371 (c)(1),
(2) Date: Feb. 28, 2022

(87) PCT Pub. No.: WO2021/038406
PCT Pub. Date: Mar. 4, 2021

(65) Prior Publication Data
US 2022/0332664 A1    Oct. 20, 2022

(30) Foreign Application Priority Data

Aug. 27, 2019    (IT) .................... 102019000015066

(51) Int. Cl.
*C07C 2/00*    (2006.01)
*C07C 2/86*    (2006.01)
*C07C 7/163*   (2006.01)

(52) U.S. Cl.
CPC .............. *C07C 2/864* (2013.01); *C07C 7/163* (2013.01); *C07C 2529/70* (2013.01)

(58) Field of Classification Search
CPC ....... C07C 15/085; C07C 2/864; C07C 6/126; C07C 7/163; C07C 2529/70
See application file for complete search history.

(56) References Cited

U.S. PATENT DOCUMENTS

| 6,313,362 | B1 * | 11/2001 | Green .................... C07C 15/085 585/323 |
| 6,512,153 | B1 | 1/2003 | Cappellazzo et al. |
| 7,371,910 | B2 | 5/2008 | Yeh et al. |
| 8,658,553 | B2 | 2/2014 | Bencini et al. |
| 9,096,488 | B2 | 8/2015 | Calaresu et al. |
| 9,259,722 | B2 | 2/2016 | Birkhoff et al. |
| 2007/0112240 | A1 | 5/2007 | Brown et al. |
| 2008/0167508 | A1 * | 7/2008 | Clark ..................... C07C 6/126 585/446 |
| 2011/0201858 | A1 | 8/2011 | Hwang et al. |
| 2011/0218366 | A1 | 9/2011 | Lorenzoni et al. |

FOREIGN PATENT DOCUMENTS

| CN | 101454426 A | 6/2009 |
| CN | 102177110 A | 9/2011 |
| CN | 105611997 A | 5/2016 |
| EP | 0563327 A1 | 10/1993 |
| EP | 0571701 A1 | 12/1993 |
| EP | 0847802 A1 | 6/1998 |
| EP | 1069100 A1 | 1/2001 |
| EP | 1257517 A1 | 11/2002 |
| WO | 8912613 A1 | 12/1989 |
| WO | 0035836 A1 | 6/2000 |
| WO | 03074452 A1 | 9/2003 |
| WO | 2006107452 A1 | 10/2006 |
| WO | 2009046977 A1 | 4/2009 |
| WO | 2012175614 A1 | 12/2012 |
| WO | 2015056167 A1 | 4/2015 |
| WO | 2016099715 A1 | 6/2016 |
| WO | 2017065771 A1 | 4/2017 |
| WO | 2017144337 A1 | 8/2017 |

OTHER PUBLICATIONS

Andrew James Smith et al. "Skeletal Metal Catalysts", Handbook of Heterogeneous Catalysis, Wiley-VCH, 2008, vol. 7, No. 2.3, pp. 94-100.
Brochure UOP Versal Alumina, A Family of High Performance Powders, A Honeywell Company, UOP5502, Apr. 2012, pp. 1-12.
Caralo Perego et al. "Recent advances in the industrial alkylation of aromatics: new catalysis and new processes", Catalysis Today, 2002, vol. 73, pp. 3-22.
Carlo Perego et al. "Combining alkylation and transalkylation for alkylaromatc production", Gree Chem, The Royal Society of Chemistry, 2004, vol. 6, pp. 274-279.
Hans-Ulrich Blaser et al. "Selective Hydrogenaton of Functionalized Hydrocarbons", Handbook of Heterogeneous Catalysis, Wiley-VCH, 2008, vol. 7, No. 14.10, pp. 3284-3294.
International Search Report dated Nov. 6, 2020 re: Application No. PCT/IB2020/057864, pp. 1-3, citing: WO 00/35836 A1, EP 0 571 701 A1, WO 89/12613 A1.
Ram Prasad et al. "Applications and Preparation Methods of Copper Chromite Catalysts: A Review", Bulletin of Chemical Reaction Engineering & Catalysis, 2011, vol. 6, No. 2, pp. 63-113.
Thomas F. Degnan, Jr. "Alkylation of aromatics with ethylene and propylene: recent development in commerical processes", Appliied Catalysis A: General, 2001, vol. 221, pp. 283-294.
Written Opinion dated Nov. 6, 2020 re: Application No. PCT/IB2020/057864, pp. 1-7, citing: WO 00/35836 A1, EP 0 571 701 A1, WO 89/12613 A1.
Chinese Office Action for Chinese Application No. 202080059689.9, dated Sep. 29, 2023, 15 pages with translation.

* cited by examiner

*Primary Examiner* — Sharon Pregler
(74) *Attorney, Agent, or Firm* — CANTOR COLBURN LLP

(57) ABSTRACT

A process for treating mixtures containing polyalkylaromatic hydrocarbons, intended for transalkylation processes, includes a mild reduction with hydrogen in the presence of a suitable hydrogenation catalyst. The process also relates to a transalkylation process of polyalkylaromatic hydrocarbons having the treatment.

16 Claims, No Drawings

PROCESS FOR TREATING POLYALKYLAROMATIC HYDROCARBONS

TECHNICAL FIELD

The present disclosure relates to an improved process for treating polyalkylaromatic hydrocarbons.

In particular, the present disclosure relates to a process for treating mixtures containing polyalkylaromatic hydrocarbons deriving from alkylation of benzene or other aromatic compounds with alcohols or olefins, more particularly with alcohols, in the presence of acid catalysts, preferably comprising zeolites.

BACKGROUND

Synthesis methods of alkylaromatic hydrocarbons by alkylation of aromatic compounds in the presence of acid catalysts are well known and widely carried out industrially for the production of basic organic intermediates, such as, for example, ethylbenzene and cumene, starting products to obtain styrene and phenol and subsequently, among other compounds, polymers such as polystyrene and polycarbonates, as well as alkyl derivatives of naphthalene, etc. . . . . Said processes use olefins, alcohols or mixtures thereof as alkylating compounds.

Equally known is the fact that, although the selectivity of the alkylation reaction has been optimized, at least a part of the aromatic reactant in the alkylation reaction undergoes more than one alkylation step and produces normally undesired polyalkylated aromatic compounds. Said undesired products are subsequently separated, normally by distillation, from the monoalkylated product and from the heavy by-products and reacted with further non-alkylated aromatic reagent in the presence of acid catalysts, to form further monoalkylated product by means of the well-known transalkylation reaction.

The state of the art of the transalkylation reaction is weighty with regards to polyalkylates coming from alkylation with olefins while nothing specific has been traced for polyalkylates coming from alkylation with alcohols: the state of the art tends not to differentiate the origin of the polyalkylates.

The published European patent application EP 1069100 (in the name of the Applicant) describes an alkylation process of benzene with propylene and isopropanol (IPA), in which the water content of the reaction mixture in the liquid phase must be less than 8000 ppm. It is in fact highlighted that there is a rapid deactivation of the catalyst by using a beta zeolite-based catalyst, for high concentrations of water in the liquid phase, above 8000 ppm. Said drawback can be moderated by increasing the benzene/IPA ratio, or, with the same ratio, by increasing the olefin/alcohol ratio in the alkylating mix and consequently decreasing the water content in liquid phase as well as the ability to reuse the IPA. Finally, by recycling part of the reaction effluent benzene or by operating in a mixed phase with water at least partially in the vapour phase. In this case, however, there is a restricted operating window.

The published patent application US 2011/218366 (in the name of the Applicant) claims the use of a ZSM-12 zeolite-based catalyst in an alkylation process in gas phase for the production of cumene, which allows to operate also with a benzene/IPA ratio up to 2 without showing signs of deactivation of the catalyst. On the other hand, a drawback of the reaction in the gas phase is the conspicuous production of diisopropylbenzenes and triisopropylbenzenes with the need for an expensive transalkylation with benzene to recover cumene. In fact, the patent claims a selectivity to cumene of 82% and a selectivity to recoverable products (cumene, diisopropylbenzenes, triisopropylbenzenes) of 98.8% [0081]. This means that the products to be sent to transalkylation are 16.8%. A specific formation of 147 g of diisopropylbenzene per kg of cumene is in particular, obtained in the gas phase (190° C., 8 bar, Benzene/IPA 3.25 mol/mol).

U.S. Pat. No. 9,096,488 describes an alkylation process of benzene with IPA under trickle-flow conditions. Said conditions ensure that the catalyst (always based on ZSM-12 zeolite) does not deactivate even with Benzene/IPA ratios of 2.4. Said conditions also favour a low molar ratio of diisopropylbenzenes/cumene in the products leaving the reactor. At 190° C., 13 bar and benzene/PAH ratio=3.25 a selectivity to cumene of 92% and 51.7 g of diisopropylbenzenes per kg of produced cumene is obtained. The n-propylbenzene is 570 ppm compared to the formed cumene. In any case it should be noted that the trickle-flow conditions are achieved with a significant recycling with consequent higher energy costs compared to the first two options which highlighted no need for recycling.

As known, one of the advantages of using IPA to replace propylene in whole or in part in the benzene alkylation reaction to give cumene, consists in the possibility of thus reusing the acetone produced in the phenol production process, through its reduction to IPA and subsequent recycling to the alkylation reaction. However, the three alkylation options described above, despite having each of them some technical advantages, are often accompanied by typical disadvantages of the approach used, and in particular, all of them produce to a certain extent a quantity of polyalkylated aromatic products which make a section of transalkylation necessary downstream of the alkylation section. This is to recover the maximum possible amount of monoalkylaromatics from the polyalkylaromatics obtained in the alkylation section.

The transalkylation process is of fundamental industrial importance for optimizing the alkylation processes of aromatics which target the production of monoalkylomatics.

The state of the art concerning the optimization of transalkylation reactions, in particular, of polyethylbenzenes, for obtaining ethylbenzene, and of polysopropylbenzenes, for obtaining cumene, is weighty and essentially covers the optimization of catalysts, operating conditions and the use of absorbent agents to purify the feeds. The objectives are the maximization of the performance and the stability of the catalytic system.

The state of the art of the transalkylation reaction is weighty with regards to polyalkylates coming from alkylation with olefins, while little or nothing specific is found in relation to polyalkylates coming from alkylation with alcohols. The state of the art, especially the recent one, tends not to differentiate the origin of the polyalkylates and to include both olefin-based alkylating agents and alcohols.

The main alkylation and transalkylation processes are described in the publication C. Perego et al. "Combining alkylation and transalkylation for alkylaromatic production", Green Chem., 2004 (6), 274-279. Furthermore, it is pointed out that the use of acetone in benzene alkylation, after reducing acetone to isopropanol, constitutes a possible approach for obtaining cumene.

WO 2006107452 claims a process of transalkylation of aromatics, in particular polyisopropylbenzene (PIPB) and polyethylbenzene (PEB) without any distinction on the origin of the polyalkylates, indeed it teaches that the alkylating agents can be indifferently olefins, alcohols, aldehydes and alkyl aldehydes. The catalysts are selected from several zeolite families suitable for the purpose. There are no data on the duration of the catalyst, nor on the possible deactivation thereof over time.

In the published US patent application 2011/201858 a process for producing cumene from acetone and benzene is described, wherein the acetone is previously reduced with hydrogen in the presence of a reducing catalyst. While reporting selectivity to cumene not higher than 71%, transalkylation processes are not described, much less preliminary transalkylation treatments are reported.

EP 1257517 describes a process for preparing cumene by alkylation of benzene with isopropanol or isopropanol/propylene mixtures. The patent shows that transalkylation, suitably applicable to polyalkylates obtained by alkylation of aromatics with alcohols is a well-known reaction to the person skilled in the art.

The published international application WO 2017/065771 describes an alkylation process useful for the production of alkylaromatic compounds, in particular ethylbenzene and cumene. In the case of cumene the alkylating agent comprises propylene and/or isopropanol. The patent teaches how transalkylation is conveniently applicable to polyalkylates obtained in the alkylation reaction described, without mentioning problems relating to the transalkylation reaction itself.

Pre-treatments for the absorption of impurities in the feeds to catalyzed processes are known in the art, but the used materials often have limited absorbent capacities, making it crucial to carry out multiple regenerations in situ to at least partially restore the absorbent capacities before the operations of unloading/replacement/disposal of the materials themselves, which can make the approach unattractive from an economic point of view.

The international published application WO 2003/074452 describes methods for the abatement of impurities, in particular nitrogen compounds, in the feeds of processes catalyzed by acid zeolites, including also alkylation and transalkylation processes of aromatics. Pre-treatments by distillation, extraction and adsorption are mentioned. However, mixtures of polyalkylaromatic compounds coming from alkylation processes are not specifically considered.

WO 2016/099715 describes a material to be used as a guard bed, having improved poison absorption capacity, for feeds such as those used in alkylation and transalkylation processes of aromatics. However, the typical problems of the guard beds, such as limited absorption capacity and the need for frequent regeneration/replacement of the bed itself, remain present.

US 2007/112240 describes a pre-treatment of feed streams made up of aromatic mixtures coming from refinery processes, in order to reduce impurities of oxygenated compounds below 5 ppm. Said pre-treatment is based on absorbent materials such as alumina or molecular sieves. Alkylation or transalkylation processes are not mentioned.

Therefore, the drawbacks connected with the stability and durability of the catalytic system in a process of transalkylation of polyalkylaromatic compounds, in particular coming from alkylation reactions of aromatics with alcohols and/or olefins, more particularly, with alcohols, such as, for example, the alkylation of benzene with alkylating mixtures comprising isopropyl alcohol (IPA) do not seem to be clearly identified, nor even satisfactorily resolved.

SUMMARY

The Applicant has now surprisingly found that it is possible to significantly improve the duration of the catalyst, expressed, for example, as a time-on-stream (TOS, i.e. the period in which the catalyst is able to operate with a minimum predetermined performance), in a process of transalkylation of aromatics, by means of a simple hydrogenating treatment on the mixture to be transalkylated.

The criticality was not clearly identified in the literature of the sector. The scientific literature concerning transalkylation with zeolite-based catalysts has so far not shown that the decay of a catalyst could be slowed down or even inhibited by means of a hydrogenation pre-treatment of the mixture to be transalkylated.

It has therefore surprisingly been found that a reducing treatment with hydrogen of the mixture containing the polyalkylated aromatic compounds coming from an alkylation step of aromatic compounds, with alcohols or olefins, preferably with alcohols, even more preferably with isopropyl alcohol, allows to considerably improve the stability and the duration (for example in terms of productivity and/or time-on-stream, TOS) of the transalkylation catalyst, also managing to avoid the management and optimization of absorbent beds, overcoming the aforementioned problems.

Productivity herein refers to the mono-alkylated product and is expressed in kg of mono-alkylated product on kg of catalyst used in the reaction.

The present disclosure therefore provides a process comprising a reduction step, preferably with hydrogen, in the presence of a suitable hydrogenation catalyst, of a polyalkylated product comprising at least one polyalkylaromatic compound, said polyalkylated product being obtained in at least one step of an alkylation process of at least one aromatic compound, preferably benzene, by an alkylating agent selected from an alcohol, a primary olefin or a mixture thereof, preferably an alcohol or a mixture of an alcohol with a primary olefin.

Other aims and advantages of the disclosure may be evident in the following of the present description and in the claims.

DETAILED DESCRIPTION OF THE DISCLOSURE

For the purpose of the present description and of the following claims, the definitions of the numerical intervals always include the extreme values unless otherwise specified.

For the purpose of the present description and of the following claims, the percentages are always by weight, except for the cases in which it is not otherwise specified.

In the description of the embodiments of the present disclosure, the use of the terms "comprising" and "containing" indicates that the options described, for example concerning the steps of a method or process or the components of a product or device, are not necessarily exhaustive. It is however important to note that also the terms used herein such as "consisting" or "essentially consisting of", or analogues thereof, even if not explicitly stated are included in the meaning and scope of the terms "comprising" and "containing".

For the purpose of the present description and of the following claims, with regards to the chemical elements and the Groups they belong to, reference is made to the Periodic Table of the Elements as published by IUPAC in 2016 and using the CAS ("Chemical Abstract Service") numbering. For the purposes of the present disclosure, the reference to a group of the periodic table includes any element of said group, with the exclusion of the transuranic elements.

For the purpose of the present description and of the following claims, the meaning of terms such as at least one, at least a and at least an also includes the meaning of the indefinite articles such as one, a, an.

For the purpose of the present description and of the following claims, polyalkylaromatic compound means any aromatic compound substituted on the same ring or on more rings condensed together, with at least two alkyl groups, optionally substituted with halogen atoms, particularly fluorine. Preferred polyalkylaromatic compounds are those having from 8 to 20 carbon atoms. Preferably the aromatic and polyalkylaromatic compounds according to the present disclosure are those which do not contain heteroatoms in the aromatic rings. Typical non-limiting examples of polyalkylaromatic compounds according to the present disclosure are xylenes, 1,3,5-trimethylbenzene, 1,2-diethylbenzene, 1,3-diethylbenzene, 1,4-diethylbenzene, 4-ethyltoluene, 1,3-diisopropylbenzene, 1,4-diisopropylbenzene, 1,3,5-triisopropylbenzene, 1,4-dimethylnaphthalene, 1,7-dimethylnaphthalene, and their mixtures. Preferred polyalkylaromatic compounds are the mixtures of polyethylbenzenes and of polyisopropylbenzenes isomers which are obtained from the alkylation processes of benzene with ethyl alcohol and/or ethylene and isopropyl alcohol and/or propylene, respectively.

The polyalkylated product subjected to reduction in the process according to the present disclosure normally consists of a mixture of compounds. It can consist of one or more polyalkylaromatic compounds, or it can comprise, in addition to said at least one polyalkylaromatic compound, also other components, such as, for example, solvents or diluents, non-alkyl substituted aromatic compounds, such as benzene or naphthalene, monoalkyl substituted aromatic compounds, such as toluene, ethylbenzene, isopropylbenzene, n-propylbenzene, and any other impurities or by-products coming from the alkylation process such as water and oxygenated organic compounds, such as, for example, alcohols, acetone, benzophenone. Preferably, the polyalkylated product fed to the present process comprises from 1 to 50% by weight, preferably from 2 to 25% by weight, more preferably from 5 to 25% by weight, of polyalkylaromatic compounds and up to a maximum of 2%, preferably from 0.0010 to 0.50% by weight of oxygenated organic compounds.

In an embodiment of the present disclosure, said polyalkylated product can be further mixed with solvents, diluents, non-alkylated aromatic compounds and with any recycling products of the corresponding alkylation process before being subjected to said reduction step with hydrogen.

Suitable solvents and diluents which can be included in or added to the polyalkylated product according to the present disclosure are normally liquids that are essentially inert towards the reduction reaction such as saturated and unsaturated, preferably aromatic, hydrocarbons, having from 6 to 20 carbon atoms. According to a preferred aspect, the polyalkylated product comprises or is added with an aromatic compound which can have both the function of solvent and/or diluent, and the function of reactant in a subsequent transalkylation step, for example, benzene. In a preferred form, the polyalkylated product subjected to reduction is obtained by an alkylation process of benzene, preferably with alcohol or alcohol/olefin mixture, and is mixed with benzene to such an extent that the mixture thus obtained, subjected to reduction, contains from 40 to 90%, more preferably from 60 to 85%, by mass of benzene with respect to the overall mass of the mixture.

Said polyalkylated product is preferably a mixture (also definable as a stream if the process is performed continuously) of polyalkylaromatic compounds and other compounds, obtained as a by-product of an alkylation process of aromatic compounds, preferably benzene, with at least one alcohol, at least an olefin or a mixture of them, preferably an alcohol or a mixture of an alcohol with a primary olefin, in the presence of an acid catalyst, preferably a zeolytic based acid catalyst. As known in the literature of the sector and previously mentioned, the alkylation processes of aromatic compounds with acid catalysis involve the formation of undesired polyalkylated aromatic compounds which are separated from the desired monoalkylated product and from the other reaction by-products with distillation operations or of other type known in the art, and therefore form a polyalkylated product (or a stream) which is normally subjected to a transalkylation reaction in the presence of an excess of non-alkylated aromatic compound, to further produce monoalkylated aromatic product. Said polyalkylated product constitutes the polyalkylated product fed to the process according to the present disclosure.

The process according to the present disclosure is preferably a transalkylation process comprising, in addition to said reduction step with hydrogen, a subsequent reaction step of the polyalkylated product subjected to reduction, wherein at least one polyalkylated aromatic compound, wherein preferably the alkyl groups are ethyl or propyl, preferably at least one dialkylated aromatic compound, is reacted with a different aromatic compound, preferably non-alkylated, preferably benzene, in the presence of an acid catalyst, wherein at least a part of the alkyl substituents of said polyalkylated aromatic compound is transferred on said different aromatic compound, preferably not alkylated.

In a different embodiment, the present disclosure relates to an alkylation process of at least one aromatic compound, comprising an alkylation step of an aromatic compound by reaction with an alkylating agent selected from an olefin, an alcohol or a mixture thereof, preferably an alcohol, in the presence of a suitable acid catalyst, and at least a reduction step of the polyalkylated product obtained as a by-product, preferably with hydrogen, of the type as specified above, followed by a transalkylation step.

Alkylation processes of aromatic compounds are known and can be performed under different conditions and with different acid catalysts. They are described for example in the following patent publications or patent applications, the content of which is incorporated herein by reference: EP 1069100, US 2011/0218366, U.S. Pat. Nos. 9,096,488, 9,259,722, 7,371,910

An alkylation process of aromatic compounds can be performed industrially in a continuous, semi-continuous or discontinuous way, and in the gas phase, liquid phase or mixed phase, in order to maintain the temperature in an optimal range and reduce the underproduction of polyalkylated aromatic compounds, the catalyst can be arranged in the reactor in several layers. By way of example only, as reported in U.S. Pat. No. 6,512,153, rapid quenching (according to the most commonly used terminology) can be carried out between one layer and the other with inert solvents and/or part of the aromatics and/or part of the alkylating reagent, alcohol or olefin.

By operating properly, high aromatic/alkylating agent ratios can be obtained on the single layer, without increasing the same overall ratio, with an evident advantage on the subsequent separation and recycling of the aromatics. Temperature control can be exercised not only by quenching with reagents and/or inerts, but also by inter-cooling between the layers, for example by interposition of refrigerants. The alkylation reaction can be suitably performed in two or more reactors in series, intercooled so as to control the temperature. The feed of the olefin, alcohol and/or aromatics can be suitably partialised between the different reactors and the different reactor layers, that is, the alkylating agent and/or the aromatics are added in more than one step; optionally the alkylating agent can be diluted with the aromatics or with an inert to favour the temperature control.

The feed of the alkylating agent is in such a quantity so as to obtain an overall molar ratio [Aromatics]/[Alkylating agent] preferably between 1 and 20, more preferably between 2 and 8.

The reaction temperature is between 100° C. and 300° C., preferably between 120° C. and 230° C., the pressure is between 0.5 and 5 MPa, preferably between 1 and 4 MPa; the space velocity WHSV is between 0.1 and 200 $h^{-1}$, preferably between 1 and 10 $h^{-1}$.

It should however be noted that the combination of the temperature and pressure conditions effectively adopted must be such as to ensure that the alkylation reaction takes place at least in part in the liquid phase, and preferably occurs substantially in the liquid phase.

Typical acid catalysts for the alkylation of aromatic compounds are heterogeneous zeolite-based catalysts, which have now replaced, especially in newly designed plants, catalysts such as AlCl3-HCl, hydrofluoric acid and in general catalysts in homogeneous phase. Depending on the type of alkylation, zeolitic catalysts with different pore sizes can be used to make the reaction more selective towards the desired product. For example 10MR structures such as ZSM-5 (MFI) have been patented and used in the vapour phase. Processes in liquid phase, with 12MR zeolites, allow to considerably increase the lifetime of the catalyst. Also Y (FAU) and Beta (BEA) Zeolites are claimed and/or used industrially. For the production of cumene, a process with fixed bed technology with a Mordenite (MOR)-based catalyst is described and patented. MCM-22 (MWW) zeolites are mentioned as catalysts that produce a low concentration of di-alkylated products. A consistent list of aromatics alkylation technologies and related catalysts can be found in publications Catalysis Today 73 (2002) 3-22 (Recent advances in the industrial alkylation of aromatics: new catalyst and new processes), in Thomas F. Degnan et al., Applied Catalysis A: General Volume 221, Issues 1-2, 30 Nov. 2001, Pages 283-294 (Alkylation of aromatics with ethylene and propylene: recent developments in commercial processes) and in the aforementioned C. Perego et al., Green Chem., 2004, 6, 274-279, (Combining alkylation and transalkylation for alkylaromatic production).

The alkylation step is preferably performed with an alcohol or an alcohol/olefin mixture as an alkylating agent. Typically, ethanol and/or ethylene are used to alkylate benzene to ethylbenzene, and isopropanol and/or propylene to alkylate benzene to cumene. Suitable alcohols and/or olefins corresponding to the alkyl residue for which it is wished the introduction on the aromatic compound are used for the preparation of other alkylated aromatic compounds, according to the known principles of organic chemistry.

The product of the alkylation step is subsequently fed to one or more separation steps according to the prior art, to recover the desired alkylated product and to separate the polyalkylated aromatic compounds that are inevitably produced at least in small quantities, for their subsequent use as such or their feeding to a transalkylation process.

By way of example, the distillation of the reaction residue of the alkylation step of benzene with isopropanol allows the monoalkylate to be separated and a mixture consisting mainly of diisopropylbenzenes (e.g. 93.2%,) with traces of acetophenone to be obtained, in addition to several and heavy polyalkylated. This cut, mixed with benzene, preferably free of $H_2O$ (H2O<100 ppm), in suitable weight ratios (e.g. 20-80 by weight), generates a mixture, containing the polyalkylated product, which can be conveniently hydrogenated, for example on Copper Chromite based catalysts, before transalkylation. The comparison with the transalkylation of similar but not hydrogenated mixtures allows to highlight the benefits of the disclosure.

In accordance with the present disclosure, the polyalkylated product obtained after the separation step or steps of the mixture leaving the alkylation step, is subjected to a reducing treatment, preferably with hydrogen and a suitable reduction catalyst according to what is claimed.

In accordance with the present disclosure, the reduction step with hydrogen of the polyalkylated product is preferably performed at temperatures between 60 and 220° C., preferably between 100 and 180° C., and at hydrogen pressures between 0.1 and 5.0 MPa, preferably between 1.0 and 3.0 MPa. Said step can be performed continuously or discontinuously, in a reactor with a solid catalyst which can be in suspension or with fixed bed or fluid bed. Preferably the catalyst is with fixed bed for continuous processes and in suspension for discontinuous processes. The reduction reaction, preferably of hydrogenation, is preferably performed under conditions such as not to produce hydrogenation of the aromatic ring of the compounds that are present in the mixture. Said conditions are known to those skilled in the art, depending on the catalyst used, or can be easily identified with simple preliminary tests.

The reducing agent, preferably hydrogen, is preferably fed pure or substantially pure to said reduction step. However, it is not excluded in accordance with the present disclosure that hydrogen can also contain significant quantities of other gases, provided that they are inert towards the catalyst and the substrate to be hydrogenated, such as, for example, nitrogen, noble gases, methane, etc. Hydrogen can optionally be preheated to a temperature above room temperature. The molar ratio between hydrogen and the polyalkylaromatic compounds contained in said polyalkylated product is preferably between 0.01 and 10, more preferably between 0.1 and 5.

In the preferred case in which the process of the present disclosure is performed continuously, the space velocity (WHSV), calculated on the total volume of the feed, including any diluents, is preferably between 0.5 and 10 $h^{-1}$, more preferably between 1 and 5 $h^{-1}$, even more preferably between 1 and 3 $h^{-1}$.

The polyalkylated product, optionally supplemented with a suitable solvent, which can also coincide with the same aromatic reagent to be alkylated in a subsequent transalkylation step, is reacted with hydrogen in the presence of a suitable catalyst, under the above mentioned conditions, so that there is substantially no hydrogenation of aromatic groups or rings. The process of the present disclosure is therefore preferably performed so that in the reduction step with hydrogen the amount of aromatic rings which are hydrogenated is less than 1%, preferably less than 0.5%, even more preferably between 0 and 0.1%, with respect to the total of the aromatic rings being fed. The amount of hydrogenated aromatic rings can be determined by the expert by any of the known techniques, such as, for example, infrared, gas chromatography, etc.

In accordance with the present disclosure, the reduction with hydrogen is performed in the presence of a suitable catalyst. Suitable catalysts are the catalysts that are typically used for selective hydrogenation reactions of oxygenated organic substrates, such as, for example, Ni, Ni Raney, Pd, Pt, Cu, Copper Chromite based catalysts, etc. The term "selective" means herein that the hydrogenation reaction does not produce significant hydrogenation of the ring of the aromatic compounds that may be present. Said hydrogenation catalysts are well known in the art and commercially available. See, by way of example, the following articles in the publication "Handbook of Heterogeneous Catalysis" (2008) (eds G. Ertl, H. Knözinger, F. Schüth and J. Weitkamp):

Blaser H., Schnyder A. et al. "Selective Hydrogenation of Functionalized Hydrocarbons", and;

Smith A. J. and Wainwright M. S. "Skeletal Metal Catalysts".

Preferably, the catalyst usable in the present reduction process with hydrogen is based on copper chromite. Said catalysts are known catalysts for selective hydrogenation reactions and commercially available, as reported, for example, in the publication "PRASAD e SINGH, Bulletin of Chemical Reaction Engineering & Catalysis, p. 63-113, November. 2011", which describes applications and methods for preparing catalysts based on copper chromite.

Other catalysts based on copper and in particular copper chromite, suitable for the reduction step with hydrogen of the present disclosure, are reported, for example, in EP 563327 and WO2017/144337.

The present process proves to be particularly advantageous if the polyalkylated product comes at least for 15%, preferably for at least 40%, more preferably for at least 60% and up to 100%, from alkylation processes of aromatic compounds with an alcohol (the remaining from alkylation processes with olefin), said percentages being referred to the mass of the polyalkylated product. For example, from alkylation processes of benzene with isopropyl alcohol, preferably for at least 25%, even more preferably starting from 40%, the rest coming from alkylation processes with propylene.

Preferably, said polyalkylated product, after separation from the monoalkylated product and any higher boiling by-products, is fed to the reduction step with hydrogen without having been subjected to other treatments to decrease the content of impurities, such as, for example, purification on molecular sieves, filtration on selective membranes, other reductive treatments, which are not however excluded from the scope of the claimed process. In any case, the process according to the present disclosure is simple to apply, efficient and economically advantageous, contributing at the same time to make the alkylation processes of aromatics by means of alcohols or mixtures of alcohols and olefins with respect to the use of olefin only more effective and competitive.

The process according to the present disclosure can comprise other steps and reactions besides the aforementioned reduction step with hydrogen. In a preferred embodiment, the process of the present disclosure comprises a step of transalkylation of the aromatic compounds contained in the polyalkylated product, following its impurities reduction treatment with hydrogen.

The process according to the present disclosure therefore preferably also comprises a transalkylation step of said at least one polyalkylaromatic compound contained in the polyalkylated product, following the reduction step with hydrogen, which can be performed according to one of the various methods known to the person skilled in the art and as described for example in EP 847802 (in the name of the Applicant), the content of which is incorporated herein by reference. Transalkylation catalysts suitable for the present disclosure can be the materials known in the art, for example, zeolites in acid or proton form, used in a form suitable for fixed bed applications known to those skilled in the art, for example extruded, added with traditional binders such as, for example, alumina ($Al_2O_3$), silica ($SiO_2$), zirconium oxide, titanium oxide, preferably silica ($SiO_2$) or alumina ($Al_2O_3$) or mixtures thereof. When alumina is used as a binder, the one with a gamma alumina phase structure is preferred. Typical examples of binder alumina precursors are commercial materials based on pseudoboehmite (sometimes called boehmite) such as those marketed under the VERSAL brand (for example Versal V-250 of the UOP Company). Materials with a gamma-alumina structure are generally obtained by calcination of pseudoboehmite, as known to the expert in the art and reported, for example, in the brochure "UOP 5502, April 2012".

In many industrial applications, such as in fixed bed catalyst reactors, it is necessary that the catalyst is formed, and it is often necessary adding a binder to make the catalyst formation possible. In applications that require a formed catalyst it is important that the catalyst maintains its physical integrity during use, in fact without sufficient strength the catalyst can be damaged or degrade, creating negative consequences on the reaction and/or on the equipment. Preferably the catalysts are formed for fixed bed applications, for example spheres or pellets. At the end of said formation, the obtained "pellets" are generally subjected to calcination. The solid obtained after binding and formation can contain from 5% by weight to 90% by weight, preferably from 10% by weight to 75% by weight, more preferably from 20% by weight to 55% by weight, of binder, with respect to total weight of said zeolite-based catalyst.

Particularly useful in the transalkylation process are the catalysts based on Beta zeolite as described in EP 847802 or based on Y zeolite as described in U.S. Pat. No. 8,658,553.

Preferably, said subsequent step for the transalkylation of aromatic compounds by reaction with one or more polyalkylated aromatic compounds is catalyzed by a catalytic composition comprising a zeolite having a crystalline structure with openings consisting of 12 tetrahedrons (wide-pore zeolites) and, as an inorganic binder, γ-alumina, preferably said composition being characterized by a pore volume, obtained by adding the fractions of mesoporosity and macroporosity present in the catalytic composition itself, greater than or equal to 0.7 cc/g, where at least 30% of said volume consists of pores with a diameter greater than 100 nanometers.

Catalytic compositions containing Y or beta zeolite in acid form are preferably used. The aromatic hydrocarbon is preferably benzene. The polyalkylated aromatic hydrocarbon is preferably selected from diethylbenzene, and optionally triethylbenzene, and diisopropylbenzene, and optionally triisopropylbenzene. Transalkylation of benzene with diisopropylbenzene and optionally triisopropylbenzene to give cumene is particularly preferred.

The transalkylation reaction must be performed under conditions such as to take place at least partially in liquid phase and preferably under conditions such as to take place substantially in liquid phase. It is preferably performed at a temperature between 150 and 300° C., at a pressure between 2 MPa and 5 MPa and at a space velocity (WHSV) between 0.5 and 10 $h^{-1}$. The molar ratio between the aromatic hydrocarbon to be transalkylated and the sum of the polyalkylated aromatic hydrocarbons in the feed mixture to the transalkylation reaction can vary between 1 and 40, preferably between 3 and 30. The catalyst is normally arranged in a fixed bed and is in particular used in chamber reactors equipped with one or more fixed catalyst beds.

A further aspect of the present disclosure is also constituted by a process for preparing monoalkylated aromatic hydrocarbons which comprises:

a) contacting and reacting under alkylation conditions, in the presence of an alkylation acid catalyst, an aromatic hydrocarbon and at least one alcohol and/or at least one primary olefin, preferably an alcohol or a mixture of alcohol and primary olefin, more preferably an alcohol, said alcohol and olefin having from 2 to 4, preferably 3 carbon atoms;

b) separating the reaction product obtained in step a) into a fraction containing the aromatic hydrocarbon not reacted in step a), a fraction containing a monoalkylated aromatic hydrocarbon, a fraction comprising a polyalkylated product comprising at least one polyalkylaromatic compound, preferably containing at least 60% by weight of dialkylated aromatic hydrocarbons;

c) subjecting said fraction comprising a polyalkylated product, obtained in step b) to a reduction step with hydrogen in the presence of a suitable hydrogenation catalyst to obtain a reduced polyalkylated product;

d) reacting said reduced polyalkylated product, obtained in step c), with an aromatic hydrocarbon, preferably the same that was reacted in step (a), under transalkylation conditions, in the presence of a suitable acid catalyst, preferably selected between a beta zeolite or a Y zeolite.

In the alkylation step a) a solid acid catalyst containing a zeolite of the medium or large pores class is preferably used. Zeolites preferably used in the catalytic composition used in the alkylation step are the zeolite with MWW (MCM-22) structure among the medium-pore structures and the BEA (beta) FAU (Y zeolite) and MTW (ZSM-12) structures among the large-pore structures, as described, for example, in WO2015056167 and WO2012175614. Beta or ZSM-12 zeolite are preferably used, even more preferably ZSM-12 as described, for example, in WO2015/056167.

The alcohol which is preferably used in the alkylation step is selected from ethanol and isopropanol. The aromatic hydrocarbon used in the alkylation step is preferably benzene. It is a particularly preferred aspect that in the alkylation step (a) benzene and isopropanol are brought into contact in the presence of beta zeolite or Y zeolite or ZSM-12.

The step (a), according to what has been previously described, can be performed in a substantially gas, substantially liquid or mixed, phase, preferably in a co-current or trickle bed.

The separation of the fractions in step b) is normally carried out by distillation according to the known methods. In particular, for example, when the alkylation product is obtained by the alkylation reaction of benzene with ethanol or isopropanol, respectively, or with an ethanol or isopropanol mixture and the corresponding olefin, in step (b) the first fraction will contain benzene, the second one will contain ethylbenzene or, respectively, cumene, the third one will be mainly formed by diethylbenzenes or diisopropylbenzenes and the last fraction is formed by a mixture of heavy hydrocarbons having a boiling point greater than or equal to 260° C.-300° C.

The third fraction, which substantially forms the polyalkylated product comprising at least one polyalkylaromatic compound (for example a mixture mainly formed by dialkylbenzenes, with less than 10% of trialkylbenzenes), optionally supplemented with a suitable volume of the same aromatic hydrocarbon of step (a), in step (c), is placed in contact with a selective hydrogenation catalyst, preferably selected from Ni, Ni Raney, Pd, Pt, Cu and Copper Chromite based catalysts.

Preferably, the reduction step with hydrogen (c) is performed at temperatures between 60 and 220° C., preferably between 100 and 180° C., and at hydrogen pressures between 0.1 and 5.0 MPa, preferably between 1.0 and 3.0 MPa.

The transalkylation step d) is performed in the presence of an acid catalyst, preferably containing beta or Y zeolite, under transalkylation conditions according to what has been previously described, preferably in at least partially liquid phase.

Preferably, said steps (c) or (c) and (d) of the aforesaid process are performed in agreement with or coincide with the process according to claim 1 or claim 8 respectively.

In order to better understand the present disclosure and to put it into practice, some illustrative and non-limiting examples thereof are reported below.

EXAMPLES

Reagents and Catalysts

Hydrogenation catalyst: Commercial catalyst called BASF 1230 based on Copper Chromite (extruded in 1/16-inch trilobes with the following composition: barium oxide 7-10%, copper oxide 15-25%, chromium oxide (III) 25-50%), produced by BASF GMbH;

Hydrogen: (Supplier Sapio purity 99.95%);

Benzene: product Sigma Aldrich, code 319953, purity>99%.

Chromatographic analysis: the gas chromatographic analyses reported herein were obtained using a Focus gas chromatograph by Thermo Electron equipped with a 25 m HP1 column.

The conditions applied for the chromatographic analysis are as follows:

Carrier gas: helium

Column: HP1—25 m capillary—internal diameter 0.32 mm, film thickness 0.52 μm

Oven temperatures: −40° C. for 2′, 45″

−10° C./min up to 290° C.

−290° C. for 5′

Detector: FID

Determination of water content: by means of Metrohm's Karl Fischer 701 instrument.

Preparation Example A

An extruded beta zeolite based catalyst, suitable for alkylation and transalkylation reactions of aromatic compounds, was prepared as described in Example 4 of the published European Patent EP 847802, incorporated herein by reference.

In particular, 58.8 g of tetraethylammonium hydroxide at 40% by weight in aqueous solution and 1.9 g of sodium aluminate (56% of $Al_2O_3$) are added to 58.4 g of demineralized water. It is heated to about 80° C. and is left under stirring until completely dissolved. The clear solution thus obtained is added to 37.5 g of colloidal Ludox HS silica at 40% by weight of SiO2. A homogeneous suspension is obtained, having a pH equal to 14, which is loaded into a steel autoclave and crystallized under hydrothermal conditions at 150° C. for 10 days, under static conditions and at autogenous pressure. The crystallized product is separated by filtration, redispersed in demineralized water (about 150 g) and re-filtered: a wet zeolite panel is obtained which still contains significant quantities of organic templating agent tetraethylammonium and sodium.

The wet panel is redispersed in an aqueous solution of ammonium acetate (200 g of water and 16 g of ammonium acetate) for ion exchange. This suspension is heated under stirring for about an hour at 80° C. The suspension is then filtered and the solid obtained redispersed in demineralized water (150 cc) for washing. The suspension is then re-filtered obtaining a wet beta zeolite panel in ammonium/alkylammonium form.

Upon the elementary chemical analysis, the sodium residue in this last sample is in fact equal to 112 ppm. The aluminum content is equal to 3.38% [Al]/[Na]=257).

The solid thus obtained (wet beta zeolite in ammonia form containing organic templating agent) was pre-mixed with a quantity of pseudo-bohemite as a precursor of gamma-alumina binder so as to obtain a binder content of 50% by weight in the solid after calcination and a solution of acetic acid as a peptizing agent, and subsequently extruded. The solid thus obtained was calcined in air atmosphere for 2 hours at 350° C. and subsequently for another 3 hours at 550° C. After calcination, an extruded catalyst of zeolite and alumina (gamma) in a mutual weight ratio equal to 50:50 is obtained. The catalyst thus obtained is characterized by a fraction of pores with a radius>100 Å greater than 35%, while the total volume of EPV extrazeolytic pores is equal to 0.81 ml/g.

Example 1 (Pre-Hydrogenation)

From an alkylation process of benzene with isopropyl alcohol (IPA) to produce cumene, a primer mixture containing polyalkylated aromatic compounds was obtained by distillation, which constitutes a polyalkylated product according to the present disclosure.

A liquid mixture (Mixture A) obtained by mixing in a ratio of about 4/1 by weight benzene and said polyalkylated product was fed up-flow to a continuous fixed bed reactor (length 25 cm, section 1 cm), containing 22.9 g of hydrogenation catalyst Cu-1230E 1/16 (BASF). Said Mixture A shows the composition shown in Table 1 below under the gas chromatograph.

TABLE 1

| Compound | Mixture A (% weight) | Mixture B (% weight) |
|---|---|---|
| Benzene | 78.50 | 78.23 |
| Ethylbenzene | 0.02 | 0.03 |
| Cumene | 0.02 | 0.02 |
| m-Diisopropylbenzene | 4.30 | 4.42 |
| o-Diisopropylbenzene | 0.08 | 0.10 |
| p-Diisopropylbenzene | 16.20 | 16.40 |
| Acetophenone | 0.03 | <0.001 |
| Phenylbenzene + High boiling | 0.85 | 0.79 |
| $H_2O$ | <0.001 | 0.005 |

In Table 1, the term "high boiling" means all the compounds which in the gas chromatographic analysis elute after the diisopropylbenzenes until the end of the analysis.

The reactor was operated in an up-flow regime at T=120° C., P=20 bar $H_2$, WHSV=2 $h^{-1}$, obtaining a hydrogenated mixture (Mixture B) at the output having the composition shown in the third column of Table 1. The substantial reduction in the acetophenone content during the reaction can be noted. It is also to be noted that under the reaction conditions adopted, the aromatic compounds do not undergo substantially hydrogenation of the aromatic ring.

Example 2

Transalkylation tests of diisopropylbenzenes were performed continuously in a spiral fixed bed reactor in an up-flow regime (tube length 5 m, section 2.98 mm), heated by forced circulation of air inside a thermostatically controlled chamber. A pneumatic valve at the outlet from the oven regulates the pressure inside the system. The reagents are stored in a steel tank (25 litres of capacity). The tank is saturated with nitrogen to avoid possible oxidation of the reagents. The reaction effluents are sampled and analysed periodically by gas chromatography and determination of the water content according to the previously reported methods.

The hydrogenated mixture (Mixture B in Table 1) obtained in accordance with the previous example 1 was subjected to transalkylation in said reactor, setting the thermostat at 220° C., with hydrogen pressure of 2 MPa and WHSV of 5 $h^{-1}$, using 12.7 g of the extruded beta zeolite based catalyst, prepared as described in the previous Preparation Example A.

The transalkylation reaction was performed for over 200 hours of time-on-stream, corresponding to the productivities and conversions reported in Table 2. As it can be observed, in this period of time the catalyst does not show significant signs of deactivation.

TABLE 2

| Time (h) | Conversion of diisopropylbenzene (%) | Cumene yield (%) |
|---|---|---|
| 43 | 86.8 | 76.9 |
| 163 | 87.6 | 77.4 |
| 235 | 86.6 | 77.1 |

The conversion of diisopropylbenzene is the percentage ratio in moles between converted and fed diisopropylbenzene. Cumene yield is the percentage ratio in moles between produced cumene and fed diisopropylbenzene Example 3 (Comparative)

On the same reactor, with the same catalytic system and under the same conditions used in the previous Example 2, the mixture to be transalkylated fed to the reactor was changed, using the non-pre-treated mixture (Mixture A of Table 1). Table 3 shows the trend of the conversion of diisopropylbenzenes and in the cumene yield which clearly tend to decrease over time.

TABLE 3

| Time (h) | Conversion of diisopropylbenzene (%) | Cumene yield (%) |
|---|---|---|
| 22 | 82.2 | 73.1 |
| 47 | 81.7 | 72.8 |
| 95 | 81.2 | 72.0 |

From what has been reported it is therefore evident that a reduction pre-treatment of the mixture to be transalkylated, preferably coming from alkylation with IPA, surprisingly with respect to the state of the art, allows to improve the stability of the catalytic transalkylation system by eliminating or in any case making the need for applying regeneration processes known to those skilled in the art less frequent.

The invention claimed is:

1. A process comprising a reduction step with hydrogen in the presence of a hydrogenation catalyst of oxygenated organic substrates, of a polyalkylated product comprising at least one polyalkylaromatic compound, said polyalkylated product obtained in at least one step of an alkylation process of at least one aromatic compound, by an alkylating agent selected from an alcohol, a primary olefin or a mixture thereof, wherein in the reduction step with hydrogen, the amount of aromatic rings that are hydrogenated is less than 1% by mass.

2. The process according to claim 1, wherein said polyalkylated product comprises at least one polyethylbenzene or at least one polyisopropylbenzene.

3. The process according to claim 1, wherein the hydrogenation catalyst is selected from Ni, Ni Raney, Pd, Pt, Cu based catalysts.

4. The process according to claim 1, wherein said reduction step is performed at temperatures between 60 and 220° C., and at hydrogen pressures between 0.1 and 5.0 MPa.

5. The process according to claim 1, wherein said polyalkylated product comprising 15-100 mass % polyalkylated aromatics.

6. The process according to claim 1, wherein said polyalkylated product is obtained from a benzene alkylation process and is mixed with benzene before the reduction step with hydrogen, to such an extent that the mixture thus obtained contains from 40 to 90%, by mass of benzene with respect to the mass of the mixture itself.

7. The process according to claim 1, comprising, downstream of the reduction step with hydrogen, a transalkylation step of the aromatic compounds contained in the polyalkylated product subject to reduction.

8. The process according to the preceding claim 7, wherein said transalkylation step is performed in the presence of a beta zeolite or Y zeolite catalyst.

9. The process according to claim 7, wherein said transalkylation step is performed at a temperature between 150 and 300° C., at a pressure between 2 MPa and 5 MPa and at a space velocity (WHSV) between 0.5 and 10 h$^{-1}$.

10. The process for preparing monoalkylated aromatic hydrocarbons, which comprises:
   a) contacting and reacting under alkylation conditions, in the presence of an alkylation acid catalyst, an aromatic hydrocarbon and at least one alcohol or at least one primary olefin, a mixture of alcohol and primary olefin, said alcohol and olefin having from 2 to 4 carbon atoms;
   b) separating the reaction product obtained in step (a) into a fraction containing the aromatic hydrocarbon not reacted in step (a), a fraction containing a monoalkylated aromatic hydrocarbon, a fraction comprising a polyalkylated product comprising at least one polyalkylaromatic compound, containing at least 60% by weight of dialkylated aromatic hydrocarbons;
   c) subjecting said fraction comprising a polyalkylated product, obtained in step (b) to a reduction step with hydrogen in the presence of a hydrogenation catalyst to obtain a reduced polyalkylated product;
   d) reacting said reduced polyalkylated product, obtained in step (c), with an aromatic hydrocarbon, the same that was reacted in step (a), under transalkylation conditions, in the presence of an acid catalyst, selected between a beta zeolite or a Y zeolite.

11. The process according to claim 10, wherein said hydrogenation catalyst in step c) is a hydrogenation catalyst of oxygenated organic substrates, selected from Ni, Ni Raney, Pd, Pt, Cu based catalysts.

12. The process according to claim 10, wherein said reduction step c) is performed at temperatures between 60 and 220° C., and at hydrogen pressures between 0.1 and 5.0 MPa.

13. The process according to claim 10, wherein said alcohol is ethanol or isopropanol and said aromatic hydrocarbon in step a) is benzene.

14. The process according to claim 10, wherein said aromatic hydrocarbon in step d) is a non-alkylated aromatic hydrocarbon.

15. The process according to claim 10, wherein said step c) is performed in agreement with or coincides with a process comprising a reduction step with hydrogen in the presence of a hydrogenation catalyst, of a polyalkylated product comprising at least one polyalkylaromatic compound, said polyalkylated product obtained in at least one step of an alkylation process of at least one aromatic compound, by an alkylating agent selected from an alcohol, a primary olefin or a mixture thereof.

16. The process according to claim 10, wherein said steps c) and d) are performed in agreement with or coincide with a process comprising a reduction step with hydrogen in the presence of a hydrogenation catalyst, of a polyalkylated product comprising at least one polyalkylaromatic compound, said polyalkylated product obtained in at least one step of an alkylation process of at least one aromatic compound, by an alkylating agent selected from an alcohol, a primary olefin or a mixture thereof, further comprising downstream of the reduction step with hydrogen, a transalkylation step of the aromatic compounds contained in the polyalkylated product subject to reduction.

* * * * *